| United States Patent [19] | [11] Patent Number: 4,849,223 |
|---|---|
| Pratt et al. | [45] Date of Patent: Jul. 18, 1989 |

[54] ANTIMICROBIAL COMPOSITIONS CONSISTING OF METALLIC SILVER COMBINED WITH TITANIUM OXIDE OR TANTALUM OXIDE

[75] Inventors: Allin S. Pratt, Wallingford; Peter R. Smith, Reading, both of United Kingdom

[73] Assignee: Johnson Matthey Public Limited Company, London, England

[21] Appl. No.: 814,413

[22] Filed: Dec. 30, 1985

[30] Foreign Application Priority Data

Dec. 28, 1984 [GB] United Kingdom ............... 8432728
Feb. 21, 1985 [GB] United Kingdom ............... 8504482

[51] Int. Cl.$^4$ .................. A61K 6/08; A61K 31/74
[52] U.S. Cl. ............................ 424/409; 424/78; 424/618; 424/617; 523/116

[58] Field of Search ........................... 523/116

[56] References Cited

U.S. PATENT DOCUMENTS

| 3,973,972 | 8/1976 | Muller | 523/116 |
|---|---|---|---|
| 4,592,920 | 6/1986 | Murtfeldt | 427/2 |
| 4,603,152 | 7/1986 | Taurin et al. | 424/131 |

*Primary Examiner*—Joseph L. Schofer
*Assistant Examiner*—Peter F. Kulkosky
*Attorney, Agent, or Firm*—Cushman, Darby & Cushman

[57] ABSTRACT

An antimicrobial composition which includes silver as the antimicrobial agent also includes a hydratable or hydrated oxide as a promoter to enhance the antimicrobial effect. Such compositions may be used to coat appliances such as catheters or may be incorporated in bone cements.

11 Claims, No Drawings

ANTIMICROBIAL COMPOSITIONS CONSISTING OF METALLIC SILVER COMBINED WITH TITANIUM OXIDE OR TANTALUM OXIDE

This invention relates to antimicrobial compositions and to medical and other appliances coated or impregnated with such compositions, and to bone cement mixtures which contain such compositions.

The use of medical and other, for example veterinary, appliances in contact with biochemical fluids, by which is meant to include protein-containing liquids such as blood, urine, milk and the like, is known to promote bacterial infection. Indeed, materials such as foodstuffs and oil-based products, are susceptible to spontaneous bacterial infection. In the case of medical appliances comprising catheters, for example urethral catheters for removal of urine, bacterial infections often result in complicating conditions which are the cause of considerable discomfort to the patient. This is the case irrespective of whether the catheterisation is of intermittent or long-term duration.

The use of silver compounds and metallic silver as bactericidal, or antimicrobial, agents in a variety of applications, in particular in the provision of an antimicrobial coating on surgical implants, has been proposed, such that the silver erodes in vivo to provide release of silver ions at a concentration sufficient to produce a localized antimicrobial effect but insufficient to cause significant damage to connective tissue—see, for example, international patent application No. WO81/02667. Furthermore, the silver may be combined with a more noble metal to promote galvanic action (see the above international application) or with a substance such as titanium or carbon (see W. German patent application No. DE 3228849 A 1). It has also been proposed to provide an antimicrobial composition for application for example to catheters, the composition comprising a mixture of an oligodynamic antimicrobial metal compound, for example of silver, and a resin (see international patent application No. WO84/01721). However, it is apparent that under certain circumstances all these prior proposals are unreliable in that the antimicrobial effect is either insufficiently strong and/or is not sustainable over a sufficiently long period of time, particularly in contact with body fluids which are aggressive, that is, where there is present a high concentration of blood, protein, synovial fluid and the like, all of which provide ideal conditions for the onset and propagation of bacterial infections. Certain resins and polymers, on the other hand, have a tendency to mask or destroy the bactericidal effect of silver or a silver compound when incorporated therein.

Bone cements are used inter alia in orthopaedic surgery for the fixing of implants and especially endoprosthetic implants in hard tissue and also as fillers for the repair of hard tissue. They are generally based on acrylic components, such that the cured cement contains poly(methacrylic acid esters) as its main ingredient, and may optionally contain a radio-opacifying filler. A typical bone cement mixture, before curing, contains an acrylic copolymer powder, for example a polymethylmethacrylate/styrene copolymer, an acrylic monomer, for example methylmethacrylate, in which the weight ratio of polymer to monomer is 2:1, and 10% by weight of a radio-opacifying filler, based on the powder component. Bone cements, whether used for fixing implants in hard tissue or as fillers for repair purposes, are generally required to remain in place for many years and therefore need to be non-degradable and inert in body fluids, particularly in such aggressive environments as are to be found in the sciatical region, for example. The onset and propagation of bacterial infections in such regions cause loosening of the implant or the repair, swelling, pain and general discomfort and may ultimately require more radical treatment such as amputation of an affected limb, for example.

In order to guard against bacterial infection, it has been proposed to render bone cements anti-bacterial or anti-microbial by incorporating therein, as partial or total replacement for the radio-opacifying filler, a bactericide. Silver as a known bactericide is not sufficiently able at ordinary concentrations to withstand aggressive environments and quickly becomes deactivated. Even promoted forms of silver are not capable of rendering a bone cement bactericidally active in aggressive environments.

It is therefore an object of the present invention to provide an antimicrobial composition for application to medical and other appliances, or for incorporation in bone cement mixtures, and which gives a sustained antimicrobial effect even in aggressive environments and/or when incorporated in certain resins or polymers which tend to mask or destroy the effect.

According to the present invention, therefore, we provide an antimicrobial composition comprising an oligodynamic metal component as the antimicrobial agent, characterised in that the composition includes a hydratable or hydrated oxide component to enhance the antimicrobial effect.

The invention also provides a medical or other appliance coated or impregnated with an antimicrobial composition comprising an oligodynamic metal component as the antimicrobial agent, characterised in that the composition includes a hydratable or hydrated oxide component, whereby in use the metal component is capable of providing release of metal ions into surrounding fluids or tissues sufficient to produce therein a sustained antimicrobial effect.

The invention also provides a bone cement mixture comprising an acrylic powder, an acrylic monomer and a filler, characterised in that the filler includes an antimicrobial composition comprising an oligodynamic metal component as the antimicrobial agent and a hydratable or hydrated oxide component, whereby in use the metal component is capable of providing release of metal ions into surrounding fluids or tissues sufficient to produce therein a sustained antimicrobial effect.

Preferably the oligodynamic metal comprises silver. The hydratable or hydrated oxide component, which in use should be in the hydrated condition, is formed preferably from an element selected from calcium, magnesium, niobium, silicon, tantalum, tin, titanium, zinc, aluminium, zirconium, cobalt, hafnium, lanthanum, tungsten and cerium. As well as providing the desired enhancement of the antimicrobial effect, hydrated oxides for use according to the invention should, of course, not produce any substantial adverse reaction in biological systems and in particular in body fluids and tissues. Particularly preferred elements are aluminium, silicon, magnesium, niobium, tantalum, titanium, tin and zinc. In particular, the use of oxides of aluminium, titanium, tin and zinc have electron densities and lattice properties such that they stabilize, under certain circumstances, the silver component as $Ag^+$ whereas more generally it is present in the metallic form.

For the purposes of the present invention, calcium hydroxyapatite is regarded as a hydrated oxide of calcium although it is strictly speaking a hydrated complex oxy-anion of phosphorus compound.

Antimicrobial compositions according to the invention when applied to a medical or other appliance may be formed as a coating or layer on the appliance or may be impregnated into at least the surface of the appliance. When so applied, the coating, layer or impregnation may extend over substantially the entire surface of the appliance or may be applied to a part of the surface, which may include the exterior and/or the interior surface.

By "medical or other appliance" we mean to include such items as catheters, wires, shunts, cannulae, enteral feeding tubes, endotracheal tubes, percutaneous devices, endoprosthetic implants, orthopaedic pins, dental prostheses, sutures, wound dressings and tubing and apparatus for use in contact with biochemical fluids, such as medical ventilator tubing.

In antimicrobial compositions according to the invention, the silver is present in the metallic form, optionally as an admixture or alloy with a more electropositive or more noble metal, or carbon, to promote galvanic action to aid release of silver ions and thus enhance the antimicrobial activity of the composition.

The hydratable or hydrated oxide may provide an electrochemical driving force to enhance the antimicrobial effect, by promoting the reaction $Ag - Ag^+$, and/or may provide an inorganic pathway which facilitates in vivo release of silver ions at a rate sufficient to overcome the effect of relatively high concentrations of blood, protein, synovial fluid and the like without causing release of silver ions at such a rate that damage is caused to local connective tissue, or may stabilise the silver as $Ag^+$.

One way of applying compositions according to the invention to an appliance is to disperse the composition in a polymeric material or precursor thereof and to apply or incorporate the resulting composition to or in an appliance surface, optionally followed by curing to complete the polymerisation. Accordingly, the invention also includes an antimicrobial composition comprising an effective amount of an oligodynamic metal, preferably silver, as the antimicrobial agent, characterised in that the composition includes a hydratable or hydrated oxide component and is dispersed in a polymeric material or a precursor thereof, such as a monomer or a pre-polymer.

Appliances to which compositions according to the invention may be applied may comprise tubing, preferably having a flexible wall, for example formed from polyvinylchloride, silicone rubber, latex, or a layered substrate, for example siliconised latex, such as is suitable for a urethral catheter. Where the composition according to the invention is formed as a coating or layer on such a substrate, the polymeric material comprises a film-forming polymer which preferably renders the coating flexible so as to be compatible with flexible-walled tubing, although chemical and biological compatibility are also required. Preferably, the polymer comprises a condensation polymer which may be substantially hydrophobic in nature. Examples of polymers which may be used include silicone rubbers, polyimides, polyvinylchloride and polyesters, but it is preferred to use a polyurethane, particularly a polyether polyurethane. The film-forming polymer need not be the same or similar to the material from which the appliance is made although for reasons of adhesion and so on it may be desirable for the materials to be similar. Optionally, the appliance wall may be surface-treated before the coating composition is applied, the surface-treatment comprising for example chlorination, or an additional layer may be interposed between the wall and the coating, for the purpose of increasing adhesion. As a further option, a thin semi-permeable top coating of polymer, for example a polyurethane, may be applied to control release of silver ions, to give improved surface smoothness and/or to mask the silver from the deactivating effects of body fluids.

The silver may be in the form of any fine morphological structure such as granules, spheroids, powder and the like, preferably deposited on the hydratable or hydrated oxide. When the silver and the hydratable or hydrated oxide are present as an admixture, flake silver is preferred because it has a high geometric surface area and presents a smoother external surface than do other particulate forms when present in a polymer film. This is of general importance in medical applications and is of particular importance for urinary catheters, in that the tendency to promote formation of calculi is thereby reduced. Flake is produced by known milling techniques, in which the milling is preferably carried out in the presence of a surfactant to prevent interparticulate welding and aggregation. The surfactant should not give rise to a toxic or other undesirable response in the material or tissue with which it comes into contact.

The presence of silver in compositions according to the invention confers the additional advantage of radio-opacity.

We have found that, by way of example of the use of various oxides, titanium dioxide may be used to enhance the activity of silver in certain polymers, particularly carbon-containing polymers such as polyurethane, whereas tantalum oxide enhances the activity of silver in silicon-based polymers such as silicone rubber, thereby rendering the compositions suitable for incorporating in or coating on appliances formed from such polymers, and tantalum oxide is suitable for incorporation in bone cement mixtures. Optionally, two or more hydratable or hydrated oxides may be used together, for example titanium dioxide and tantalum oxide.

Antimicrobial compositions according to the invention and for use with medical and other appliances preferably contain from 1 to 50% by weight of silver, blanace hydratable or hydrated oxide, more preferably from 1 to 10% by weight of silver. For use in bone cements, antimicrobial compositions according to the invention preferably contain 20 to 99% by weight of silver, balance hydratable or hydrated oxide, more preferably 50 to 80% by weight of silver, for example 60%. The particle size of the oxide should preferably be below 5 microns and the surface area between 1 and 100 $m^2 g^{-1}$, more preferably between 5 and 50 $m^2 g^{\times 1}$, typically in the region of 20 $m^2 g^{-1}$. The compositions when incorporated into polymers should be present in the range 1-75% by weight, based on the total of antimicrobial composition and cured polymers, preferably 5-40% by weight, and when incorporated into bone cements should be present in the range 1 to 25% by weight, based on the acrylic powder, preferably 5-10% by weight. For example, silver may be deposited on tantalum hydroxide according to the amounts set our below and incorporated in bone cement mixtures at a level of 10% by weight, based on acrylic powder:

| Ag | Ta(OH)₅ | Ratio |
| --- | --- | --- |
| 95 | 5 | 19:1 |
| 75 | 25 | 3:1 |
| 60 | 40 | 3:2 |
| 50 | 50 | 1:1 |
| 25 | 75 | 1:3 |

The antimicrobial activity of compositions according to the invention may be assessed by measuring the zone of inhibition created by a sample in standard agar. The sample may either comprise a section of catheter carrying a coating of a composition according to the invention applied as a dispersion in a polymer, or may comprise a cured bone cement containing a composition according to the invention. The testing procedure is to prepare a culture of the chosen organism (Staphylococcus aureus) grown for 6 hours on rolling culture at 37° C. in 10 ml of tryptone soya broth (Oxoid L37). The culture is diluted 1:100 in fresh broth before use. Rings of 2 mm thickness are cut aseptically from the catheters, or discs or 6 mm diameter are prepared from a bone cement mixture containing 36 g of a polymethylmethacrylate/styrene copolymer powder, 20 g of methyl methacrylate, and 4 g of silver component dispersed on hydrated oxide in a ratio by weight of 3:2, and are placed in a sterile petri dish containing 15 ml of molten, conditioned standard agar medium. The medium consists of bacteriological peptone (5 g), purified agar (13 g), and "Analar" sodium chloride (15 g). This is made up to 1 l with distilled water, boiled to dissolve the agar, autoclaved at 121° C. and conditioned at 56° C. for 48 hours. The medium containing the sample is then allowed to set and, when dry, is inoculated by wiping a sterile swab, dipped into the diluted culture, across the surface of the agar. The inoculated medium is then incubated inverted overnight at 37° C. and the zone of inhibition of bacterial growth around each sample is measured.

Catheter samples are prepared by firstly forming an antimicrobial composition according to the invention and then dispersing in a polymer and applying to a catheter. One way of forming an antimicrobial composition according to the invention is to form a slurry of the hydratable or hydrated oxide in water, add aqueous sodium hydroxide solution to render the slurry alkaline, and add aqueous silver nitrate solution followed by formaldehyde to reduce the silver nitrate to metallic silver which deposits on the oxide particles. The composition may then be dispersed in a polymer by dissolving the polymer, or a pre-polymer or monomer, in a suitable solvent to a viscosity such that the antimicrobial composition can readily be incorporated therein, adding the antimicrobial composition in the required proportion, and dispersing, for example in a blender or triple-roll mill. The resulting dispersion may then be applied to a catheter, for example, by dipping followed by drying to remove solvent and if necessary curing to complete the polymerization.

Another way of providing antimicrobial compositions according to the invention, particularly when the hydratable or hydrated oxide is tantalum hydroxide, is to prepare hydrated tantalum oxide (known as "tantalic acid") as an inorganic polymeric oxide gel by hydrolysis of tantalum pentachloride with caustic soda according to known methods, and to dehydrate the gel to provide the oxide in non-agglomemerative, finely-divided form which may be re-dispersed in silver nitrate solution and silver precipitated as silver chloride on addition of sodium chloride. The resulting product may then be washed and dried. We believe that silver chloride is spontaneously reduced to silver metal in the presence of light. However, the silver may be stabilized as $Ag^+$, for example the chloride, by using an oxide the electron density and lattice properties of which are such that the chloride or other halide or pseudohalide phase is rendered resistant to degradation to metallic silver. It is preferred, in order to obtain this effect, to prepare the antimicrobial composition by dry impregnation, to obtain the maximum possible level of dispersion of the silver compound throughout the pores of the support. The dry impregnation technique involves adding sufficient silver nitrate solution to fill completely the pore volume, such that total absorption occurs and a dry mix results, and slurrying in saline to convert the silver nitrate to silver chloride.

We have deposited silver on silica, magnesium hydroxide, alumina tantalum hydroxide, titania, and calcium hydroxyapatite, all of which are either hydrated or hydratable oxides, and incorporated the resulting compositions according to the invention into silicone rubber, plasticised polyvinylchloride, and a polyether polyurethane ("Desmocoll" D510, Bayer). The resulting dispersions were then applied to catheters formed from polyvinylchloride by a dipping technique. Good results for inhibition of bacterial growth were observed for 2.5% silver on titania and 20% silver on titania at loadings of up to 80% by weight in polyether polyurethane, 2.5% silver on silica in silicone rubber and 2.5% silver on tantalum hydroxide in polymethylmethacrylate. Particularly encouraging was the inhibition in agar containing 3% red blood cells, for which medium silver alone is totally inactive, as described in the following example:

EXAMPLE

A filler material comprising 20% by weight of Ag on $TiO_2$ was prepared by reducing the silver oxide formed on addition of silver nitride to an alkaline slurry of $TiO_2$ with dilute formaldehyde. The resulting Ag on $TiO_2$ antimicrobial composition was spray dried.

15g of this compositions were dispersed in 25g of suitable solvent. 19g of resin comprising 17% by weight of "Desmocoll" D510 in a suitable solvent were added and the composition redispersed.

The resulting composition was applied to standard PVC catheters to form a uniform coating and then dried for 18 hours at 77° C. in vacuum.

Catheters produced by this route showed the following antimicrobial effect, where the figures relate to inhibition zone size in mm for three samples in each test:

| Organism | SAM | 3% RBC/SAM |
| --- | --- | --- |
| E coli | 25, 26, 27 | 11, 12, 12 |
| Staph. aureus | 26, 29, 31 | 13, 13, 14 |

These figures compare with figures for silver alone of 25 in SAM and 0 in 3% RBC/SAM.

For bone cements, the samples were compared with a prior art bone cement containing metallic silver with no hydratable or hydrated oxide. The diameter of the zone of inhibition was found to be 30–35 mm in standard agar for the inventive composition, compared with 25 mm for the prior art composition, and 10–12 mm in standard agar plus red blood cells for the inventive composition, compared with zero for the prior art composition.

Sample discs were also immersed in distilled water and periodically removed and re-tested in the blood/agar mixture. The zone of inhibition was observed to improve with immersion time.

Active bone cements may be prepared within a wide range of silver to hydrated tantalum oxide ratios from 19:1 to 1:9 in a concentration of from 2 to 15% by weight based on the powder component, and give results comparable to the above exemplary composition.

Bone cement compositions according to the invention exhibit mechanical and curing properties which are within the essential limits laid down in ASTM F 451 part 46.

The invention also includes cured antimicrobial bone cements comprising an acrylic polymer and a radio-opacifying filler, wherein the filler includes silver deposited on a support comprising a hydratable or hydrated oxide.

We claim:

1. An antimicrobial composition for use in contact with materials which cause or are susceptible to bacterial infection by body fluids or tissue, said composition comprising metallic silver as the antimicrobial agent together with an oxide component selected from the group consisting of titanium and tantalum oxides present in an amount effective to provide release of silver ions into surrounding tissue or fluid.

2. An antimicrobial composition according to claim 1, in which the composition is dispersed in a polymeric material.

3. An antimicrobial composition according to claim 2, in which the composition constitutes from 1 to 75% by weight, based on the total of antimicrobial composition and cured polymer.

4. An antimicrobial composition according to in which the silver is deposited on particles of titanium dioxide.

5. An antimicrobial composition according to claim 4, which the mean particle size of the oxide is below 5 microns.

6. An antimicrobial composition according to 5, in which the surface area of the oxide particles is between 1 and 100 $m^2 g^{-1}$ inclusive.

7. A medical or other appliance, characterized in that it is coated or impregnated with an antimicrobial composition according to claim 1.

8. A bone cement mixture comprising an acrylic powder, an acrylic monomer and a filler, characterized in that the filler includes an antimicrobial composition according to claim 1.

9. In an antimicrobial composition comprising metallic silver as the antimicrobial agent and wherein the activity of said agent is undesirably affected in contact with body fluids, the improvement which comprises including in said composition titanium dioxide to enhance the activity of said agent.

10. In a method wherein metallic silver is used as an antimicrobial agent in the presence of fluids which tend to undesirably affect the antimicrobial activity of the silver, the improvement which comprises including titanium dioxide with the metallic silver to stabilize the activity of the silver against said fluids and to provide release of silver ions into the fluid to produce a sustained antimicrobial effect.

11. A composition according to claim 1 including 110% silver, the balance consisting essentially of titanium dioxide.

* * * * *

UNITED STATES PATENT AND TRADEMARK OFFICE
CERTIFICATE OF CORRECTION

PATENT NO.  : 4,849,223

DATED       : July 18, 1989

INVENTOR(S) : PRATT ET AL

It is certified that error appears in the above-identified patent and that said Letters Patent is hereby corrected as shown below:

Column 8, line 34, claim 11, change "110%" to --1-10%--.

Signed and Sealed this

Third Day of April, 1990

Attest:

HARRY F. MANBECK, JR.

*Attesting Officer*    *Commissioner of Patents and Trademarks*